US007935101B2

(12) United States Patent
Muramatsu

(10) Patent No.: US 7,935,101 B2
(45) Date of Patent: May 3, 2011

(54) MULTI-CHAMBER CONTAINER

(75) Inventor: Yasuhiro Muramatsu, Shizuoka (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/436,172

(22) Filed: May 6, 2009

(65) Prior Publication Data

US 2009/0254032 A1 Oct. 8, 2009

Related U.S. Application Data

(63) Continuation of application No. PCT/JP2007/071387, filed on Nov. 2, 2007.

(30) Foreign Application Priority Data

Nov. 6, 2006 (JP) ................................ 2006-299822

(51) Int. Cl.
*A61B 19/00* (2006.01)

(52) U.S. Cl. ......... 604/410; 604/408; 604/416; 206/219

(58) Field of Classification Search .................... 604/87, 604/408, 410, 416; 206/219
See application file for complete search history.

(56) References Cited

U.S. PATENT DOCUMENTS

| | | | | |
|---|---|---|---|---|
| 4,997,083 | A * | 3/1991 | Loretti et al. | 206/219 |
| 6,017,598 | A | 1/2000 | Kreischer et al. | |
| 2004/0134802 | A1* | 7/2004 | Inoue et al. | 206/219 |
| 2005/0087456 | A1 | 4/2005 | Oka et al. | |
| 2007/0060903 | A1 | 3/2007 | Miyajima et al. | |
| 2007/0208320 | A1 | 9/2007 | Muramatsu et al. | |
| 2008/0033390 | A1 | 2/2008 | Kitagawa et al. | |
| 2008/0097372 | A1 | 4/2008 | Shimizu et al. | |

FOREIGN PATENT DOCUMENTS

EP 1 475 067 A1 11/2004

(Continued)

OTHER PUBLICATIONS

U.S. Appl. No. 12/688,427, filed Jan. 15, 2010, Muramatsu, et al.

*Primary Examiner* — Nicholas D Lucchesi
*Assistant Examiner* — Leah Stohr
(74) *Attorney, Agent, or Firm* — Oblon, Spivak, McClelland, Maier & Neustadt, L.L.P.

(57) ABSTRACT

The present invention relates to a multi-chamber medical bag, which is capable of obtaining a positive mixture of medicines, prior to the discharge thereof. A weak seal 24 is provided for dividing the space inside the medical bag 10 into the left-handed and right-handed partitions 26-1 and 26-2. The weak seal 24 has a first portion 24-1 extending between the partitions 26-1 and 26-2 and a bifurcated adjacent to and faced with an outlet port 12. Additional strong seals 30-1 and 30-2 are arranged on both sides of the second portion 24-2 and extend at right angle to the first portion 241 toward the strong seal 14 at the outer periphery of the medical bag. When the partition 26-1 or 26-2 is pressed, the resultant inflated deformation of the medical bag is mainly directed to the first portion 24-1 due to the existence of the additional strong seals 30-1 and 30-2, which allows the last portion to be separated, resulting in a mixing of the medicines in the partitions 26-1 and 26-2. The second portion 24-2 is the opened, which allows the mixed medicines to be introduced into the outlet port 12.

9 Claims, 5 Drawing Sheets

FOREIGN PATENT DOCUMENTS

| | | |
|---|---|---|
| JP | 08-511216 | 11/1996 |
| JP | 09-327498 | 12/1997 |
| JP | 2003-159310 | 6/2003 |
| JP | 2004-000661 | 1/2004 |
| JP | 2005-288022 | 10/2005 |
| JP | 2005-318997 | 11/2005 |

* cited by examiner

MULTI-CHAMBER CONTAINER

TECHNICAL FIELD

The present invention relates to a multi-chamber container, which is formed as a medical bag having a separable welded part, which divides the space in the bag into compartments for storing separately medical liquids, which are, after subjected to a mixing operation, discharged from an outlet port.

A multi-chamber container for an infusion has here-to-fore known, which has a medical bag made of soft film having opposite layers, which are welded with each at relatively low temperature, so that a weak seal (separable welded portion) is created for dividing the bag into compartments for separately storing different medical liquids. An outlet port as a molded product is connected to an outer peripheral portion of the medical bag. The outlet port is formed as a tubular shape having an inner cavity, which cavity has one end opened to one of the compartments and a second end provided with a rubber plug. Prior to the commencement of an infusion operation for giving medicines to a patient, the medical bag is outwardly pressed, which causes the weak seal to be separated and broken, so that inner cavities in the bag are communicated as a single chamber, so that the two kinds of medical liquids are mixed with each other. As a result, a piercing of the rubber plug by a needle of an infusion set allows the medicines from the medical bag to be given. In this mixing type of the multi-chamber medical container, an operation for separating the weak seal for mixing medial liquids is essential prior to the administration of the medicine. When the weak seal is maintained under non-opened condition, the piercing of the rubber plug results in an erroneous operation that the medical liquid located only at one of chambers adjacent the outlet port is given. In order to combat this problem, a medical bag has been provided, having modified configuration of a weak seal for separation of the space inside the bag into two compartments, which weak seal has a bifurcated or Λ shaped portion located in front of the outlet port. This portion of the weak seal creates a third chamber, which communicates with the outlet port, on one hand and, on the other hand, is disconnected from the medical liquid storage compartments. In other words, the weak seal for separating medical liquid storage compartments includes a V-shaped portion, by which a separation of the weak seal is promoted. See patent document No. 1.

Patent Document No. 1: Japanese Un-Examined Patent Publication No. 2004-661

DISCLOSURE OF THE INVENTION

Problem to be Solved by the Invention

In the prior art disclosed in the Patent Document No. 1, the weak seal extends along the almost entire length of the medial bag between the compartments storing the respective medical liquids and connects with the bifurcated portion for creating the third chamber. This structure of the weak seal aims to obtain a positive two staged opening operation that, prior to the separation of the bifurcated portion, the portion separating the compartments is done, firstly, for mixing the medical liquids in the compartments and, secondly, the mixed medical liquid is discharged. Namely, the portion of the weak seal extending between the medical liquid compartments is longer than the bifurcated portion. Therefore, the weak seal portion between the compartments likely generates a larger separation force upon the opening of the medical bag and, therefore, can be expected to be separated earlier than the bifurcated portion while taking a consideration that the V-shaped portion for initiating the separation operation is provided.

However, a test conducted by the inventors shows that the initial separation of the weak seal is not necessarily initiated at the portion between the partitions. The weak seal is separated by an expanded deformation of the medical bag as generated when the medical bag is subjected to a pressing force from its outside. In the prior art structure, the expanded deformation is equally transmitted not only to the portion between the partitions but also to the bifurcated portion. Therefore, it is most likely that the opening is, at first, commenced at the portion separating the partitions due to the increased length of the latter portion. It may, however, be frequently occurred that the bifurcated portion is, at first, separated, depending on the location where the pressure is applied.

In view of the above difficulties, the present invention aims to provide a new structure of a medical bag of a multi-liquid mixing type, wherein an administration is prohibited under a non-opened condition, capable of reducing the production cost as well as of increasing the efficiency during use by a user, while positively reducing a chance of occurrence of erroneous operation.

Means for Solving Problems

In the multi-chamber medical bag according to the present invention, a separable weld is for welding opposed surfaces of flexible films constructing the medical bag, so that a plurality of partitions for storing, respectively, medical fluids are formed inside the medical bag. The separable weld may, for example, have a construction that it includes a first portion between the partitions from the periphery of the medical bag to a location adjacent to and faced with the outlet port and a second portion extending from both sides of the first portion to peripheral edges of the medical bag, in order to create an intermediate chamber between the faced surface of the flexible films, which intermediate chamber is opened to the outlet port while being separated from the partitions. The second portion may, for example, have a shape bifurcated from the second portion and extends to the peripheral parts of the medical bag, astride the outlet port. The second portion is at least partially separable for obtaining a communication of mixed medicines to the outlet port as obtained by a separation of said first portion. Furthermore, a provision is made as to a restrictor of transmission of a inflated deformation of the medical bag to the separable weld, as generated by an initial pressing of medical liquid stored in the partition of the bag in a manner that the deformation is substantially instantly transmitted to the first portion and that a transmission of the deformation to the second portion is restricted or prohibited. In order to construct such a restrictor, a second weld for non-separable welding of the opposed surfaces of the films of the medical bag is, for example, provided. The second weld restricts the transmission of an inflated deformation of the medical bag to the second portion of the first weld, as generated when the medical liquid stored in the partition is pressed. The second welds, which are constructed by a non-separable welding of the opposed surfaces of the medical bag, are arranged on both sides of the outlet port so as to extend laterally, preferably, transversely from the first part of the first weld to the periphery of the medical bag. The second weld controls or restricts the transmission of the direction of inflated deformation in such a manner that the separation of the first weld occurs first and mainly at its first portion lather than its second portion.

EFFECT OF THE INVENTION

The provision of the restrictor or the second weld makes it possible that a restriction occurs in a transmission of an inflated deformation of the medical bag as generated by the outward pressing of the medical bag for opening the same, i.e., the inflated deformation is mainly directed to the first portion and is almost not transmitted to the second portion. Therefore, a separation of the first portion initially occurs, thereby positively mixing the medical liquids. Then, a further separating operation of the second portion is executed, which allows the mixed liquid to be flown into the outlet port. In short, a two-stage operation of a preceding mixing of the medicines followed by the succeeding discharge of mixed medicines is more reliably obtained, on one hand, and, on the other hand, an occurrence of such an error that the operation is proceeded under a single liquid state is reliably prevented.

BRIEF DESCRIPTION OF ATTACHED DRAWINGS

FIG. 1 is a plan view of a multi-chamber container according to the present invention.

FIGS. 2(A), 2(B), 2(C) and 2(D) are sectional views taken along lines A-A, B-B, C-C and D-D, respectively, in FIG. 1.

EXPLANATION OF REFERENCE NUMERALS

10: Medical Bag
12: Outlet Port
14: Strong Seal
20: Rubber Plug
22: Needle
24: Weak Seal (First Weld)
24-1: First Portion of Weak Seal
24-2: Second Portion of Weak Seal
26-1, 26-2: Partition
30-1, 30-2: Additional Strong Seal (Second Weld)

BEST MODE FOR PRACTICING THE INVENTION

Figure 1:
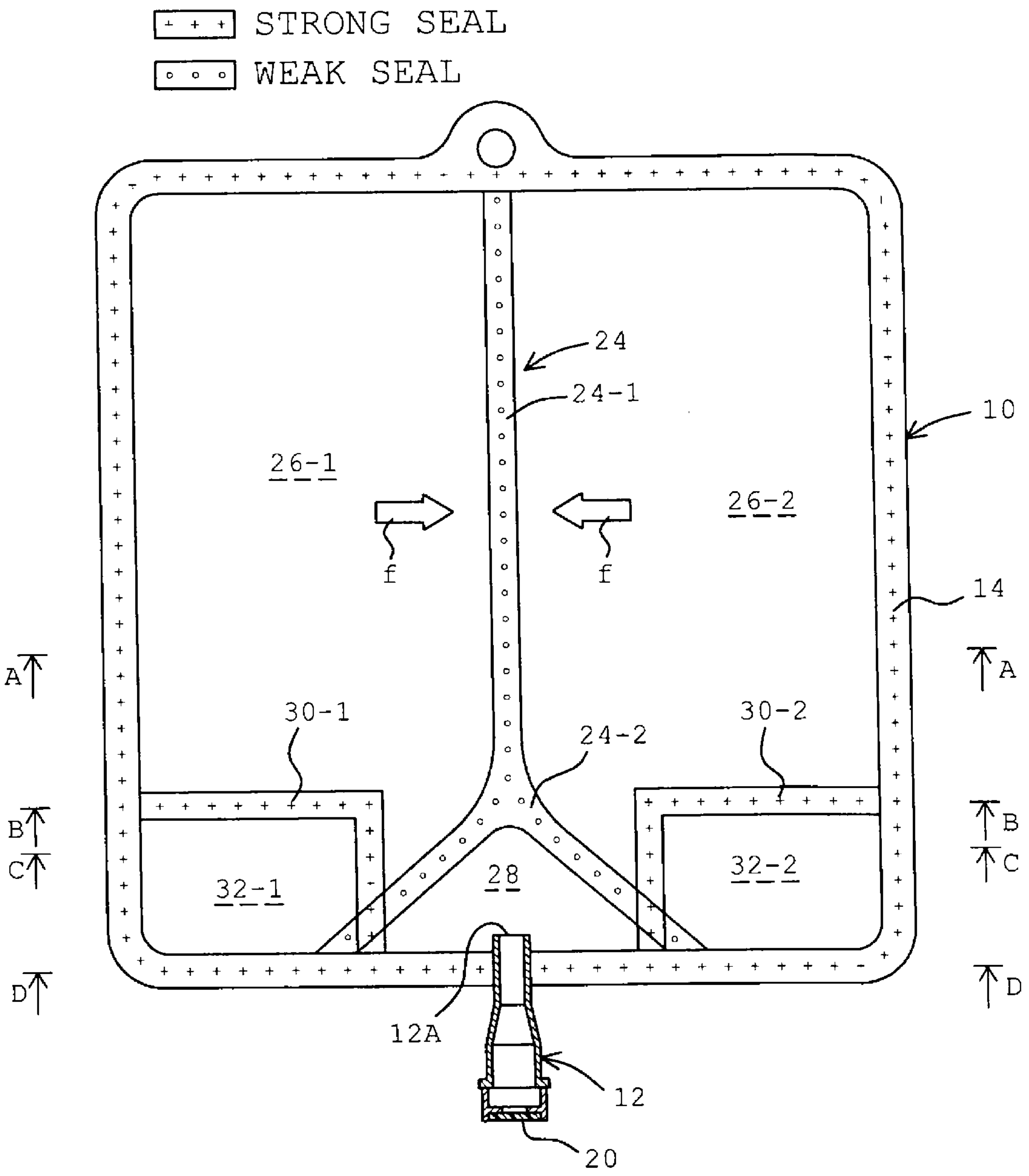

In FIG. 1, a multi-chamber container has a flattened medical bag 10 for storing medical liquids and an outlet port 12. The medical bag 10 is made of a material as a synthetic resin film (flexible film of the claimed invention), such as polyethylene film, of a multiple layer structure of a thickness of a value of, for example, 200 microns. From the synthetic resin film for constructing the medical bag 10, a pair of upper and lower cut pieces or upper and lower layers 10A and 10B are provided, which are superimposed so as to sandwich the tubular outlet port 12 (FIG. 2(D). A high temperature welding at a temperature of a value such as 130° C. in case of polyethylene film is done along the entire periphery. As a result, a strong seal 14 (non-separable weld) is obtained along the entire periphery including the portion of the tubular outlet port 12, so that a bag shape is created. The welding for obtaining the strong seal 14 is executed at a temperature of a value about 130° C. in case of polyethylene film as above. This temperature value is high enough for preventing any separation under a pressure as normally generated in the medical bag when the bag is pressed in order to open the medical bag 10. As a result, regardless of the effect of outwardly applied physical force, the liquids are maintained in the medical bag 10 without generating any leakage. The tubular outlet port 12 is made as a plastic molded produce having a wall thickness (rigidity), which is large enough to keep its tubular shape. The tubular outlet port 12 is, at its bottom end in FIG. 1, projected out of the medical bag 10. To the bottom end of the tubular outlet port 12 projected from the bottom end of the medical bag 10, a rubber plug (plug member) 20 is arranged, which plug is to be pierced by a needle of an infusion set (not shown). The medical bag 10 is made from a tubular film in place of the welded structure of the upper and bottom pierces cut from a film.

Figures 2A, 2B, 2C, 2D:
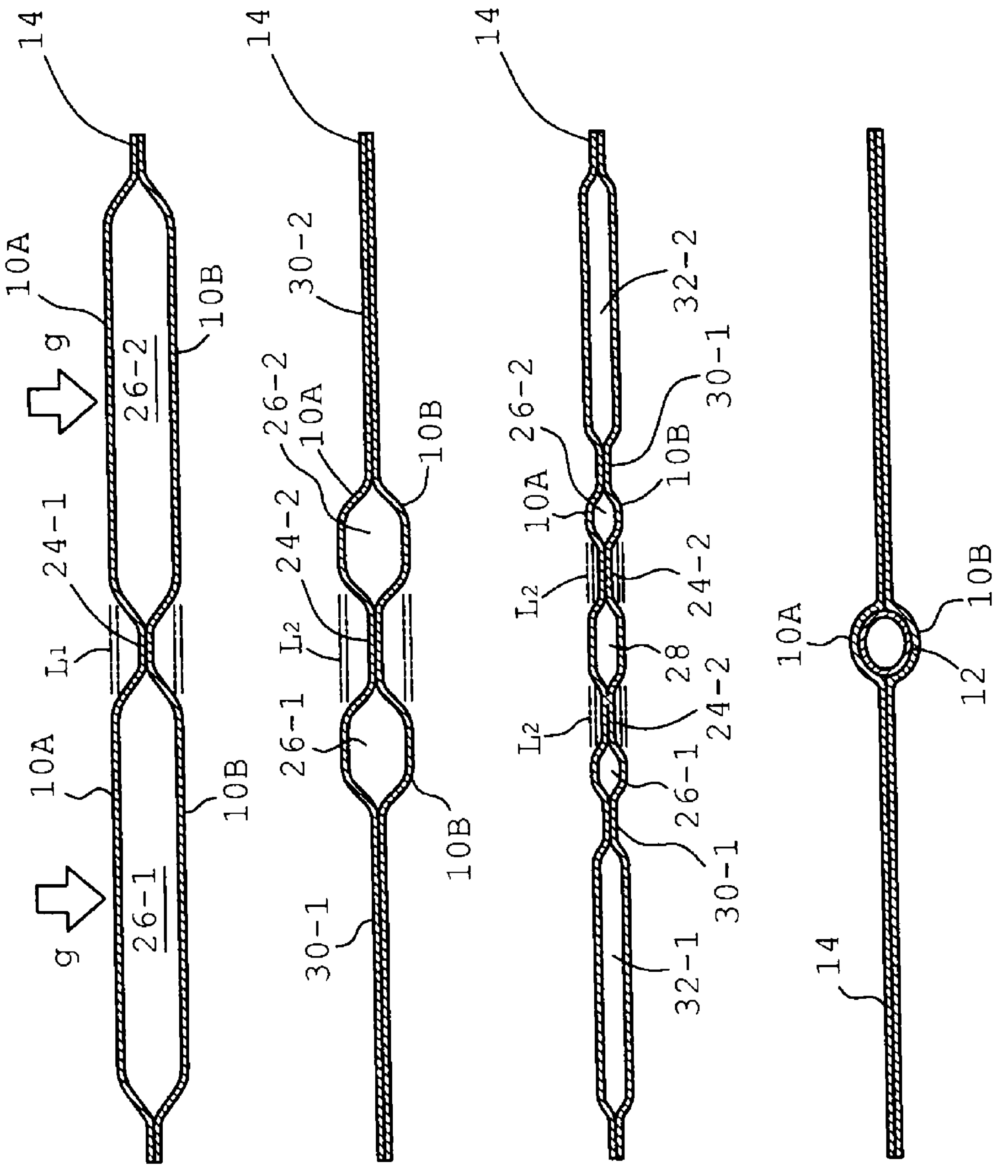

A separable welding of two pierces of a synthetic resin film 10A and 10B at the top and bottom is done in order to form a weak seal 24 (a separable weld or first weld of the claimed invention), which weak seal extends vertically at the middle of the width of the medical bag 10, in a manner that the space inside the medical bag is separated to a left-handed and a right-handed partitions 26-1 and 26-2 for storing medical liquids, respectively (FIG. 2(A)). At the weak seal 24, the degree of the welding between two pierces of a synthetic resin film at the top and bottom of the medical bag 10 is such that a capability of a pressing separation is obtained. This capability implies that a pressing of the medical bag 10 by a palm under a desired pressure for opening the bag causes the latter to be inflated due to the storage of the medical fluids therein, so that the top and bottom cut pierces 10A and 10B at the weak seal 24 are separated under the outside force as shown by phantom lines $L_1$ and $L_2$ in FIGS. 2(*a*) to 2(*c*). In case of the polyethylene of this embodiment of the invention, the welding to obtain the weak seal 24 is done at the temperature of value of 120° C., which is lower than a temperature of value of 130° C. for obtaining the strong seal 14.

In the embodiment, as shown in FIG. 1, the weak seal 24 is constructed by a first portion 24-1, which extends downwardly from the upper periphery of the medical bag between the left-handed and the right-handed partitions 26-1 and 26-2 toward the location faced with and adjacent to the open end 12A of the outlet port 12 and by a second portion 24-2 (FIGS. 2(B) and 2(C)), which extends from the first portion 24-1 bi-laterally in a bifurcates shape toward the bottom periphery of the medical bag 10, so that a third chamber 28 is created, which third chamber is separated from the partitions 26-1 and 26-2 by the second portion 24-2, while being in communication with the outlet port 12.

According to the present invention, additional strong seals 30-1 and 30-2 (FIGS. 1 and 2(B)) are provided on both sides of the outlet port 12, which strong seal is a restrictor or a second weld according to the present invention, which restricts the transmission of a force generated by an inflated deformation of the medical bag when the medical bag is opened in such a manner that the force is mainly transmitted to the first portion 24-1, while no transmission of the same to the second portion 24-1 is substantially occurs. Namely, the additional seals 30-1 and 30-2 are formed by welding the opposed faces of films constructing the medical bag at the temperature of substantially the same degree as that for obtaining the strong seal 14 at the outer periphery of the medical bag for preventing the opposed films from being separated by the outside force under the inflation of the medical bag as obtained when the latter is opened. In this embodiment, as shown in FIG. 1, the additional seals 30-1 and 30-2 extend, firstly, from the left-handed and right-handed peripheral portions (strong seal 14) of the medical bag, to locations adjacent to and faced with the weak seal 24, i.e., positions of connection between the first portion 24-1 and the second portion 24-2, in a direction transverse to the first portion 24-1, then, change direction at right angle, and, finally, extend downwardly to the bottom periphery (strong seal 14) of the medical bag after crossing the second portion 24-2 of the weak seal 24. Since the additional seals 30-1 and 30-2 are separated at the location where the outlet port 12 is provided, so that any blockage of flow of the medical fluid toward the outlet port 12 does not occur. Furthermore, the additional seals 30-1 and 30-2 divide the partitions 26-1 and 26-2, at the bottom parts, and create small chambers 32-1 and 32-2 (FIG. 2C). At a suspended condition to an infusion stand, the small chambers 32-1 and 32-2 are located at the bottom sides of the medical bag 10 and, therefore, any obstruction of a flow of the medical liquid to the outlet port 12 does not occur after the communication of the partitions 261- and 26-1 as obtained by the opening of the weak seal 24. In short, the medical liquids in the medical bag are introduced into the outlet port 12 without being remained in the bag.

In order to produce a medical bag, an upper and lower film cut pierces 10A and 10B are faced with each other and welded at a high temperature for creating strong seals 14 and 30-1 and 30-2. Then, a low temperature is done for creating a weak seal (24-1 and 24-2). The strong seal 14 at the outer periphery of the medical bag has openings, i.e., non-welded portions, which open to the partitions 26-1 and 26-1, respectively. To the partitions 26-1 and 26-1, medical fluids are filled by way of the respective openings, which are, then, welded and sealed. Furthermore, the intermediate chamber 28 is also formed with an opening, through which purified water is filled and which opening is, then, welded and sealed. Since the purified water in the intermediate chamber 28 is also opened to the outlet port 12, a subsequent sterilizing process is executed under a wet heat condition, resulting in high sterilization efficiency.

In order to execute an opening operation, the medical bag is placed, for example, on a desk and is outwardly pressed by palm at one of the partitions 26-1 and 26-2 storing the medical liquids or both as shown by arrows g (FIG. 2(A), so that the medical bag as pressed and storing the medical liquid is inflated and the resultant inflation is transmitted to the weak seal 24. As a result, a separation of the welded film layers 10A and 10B constructing the weak seal 24 is generated. In this embodiment, at locations adjacent outlet port 12, the additional strong seals 30-1 and 30-2 extend transverse to the first portion 24-1 of the weak seal 24 and are located on both sides of the second portion 24-2 of the weak seal 24. As a result, a inflated deformation of the medical bag, as obtained when the partition 26-1 or 26-2 is pressed, is mainly transmitted to the first portion 24-1 in a shown left or right direction as illustrated by arrows f due to the guiding action as obtained by the additional strong seals 30-1 and 30-2. Therefore, a separation force is large at the first portion 24-1 and is small at the second portion 24-2. Therefore, a separation at the first portion 24-1 as shown by the phantom lines $L_1$ occurs initially, which allows the medical liquids in the partitions 26-1 and 26-2 to be mixed with each other. After the mixing, the second stage pressing is done in a manner that the second portion 24-2 of the weak seal 24 is separated and opened, which allows the mixed liquid to be introduced into the outlet port 12. Since the mere separation of the first portion 24-1 of the weak seal is not enough to cause the liquid to be flown from the outlet port, the operator is reminded to proceed an additional pressing to separate the second portion 24-2 of the weak seal, so that the top and bottom film layers 10A and 10B at the second portion 24-2 are separated and opened as shown by the phantom lines $L_2$ in FIGS. 2(B) and 2(C).

In FIG. 1, the additional strong seal 30-1 or 30-2 has a vertical location, whereat, in the weak seal 24, the first portion 24-1 is connected to the second portion 24-2. However, the present invention is not limited to this arrangement and, therefore, a more lowered location than shown in the drawing is possible, so long as an operation for restricting the transmission of the inflated deformation to the second portion 24-2, as obtained when the pressing of the medical liquid stored in the partition 26-1 or 26-2, is done. As a modification, the strong seal 14 at the bottom outer periphery of the medical bag may extend as similar as the additional strong seals 30-1 or 30-2 in FIG. 1 does. In this case, the strong seal 14 itself functions as the restrictor of the transmission of the inflated deformation to the second portion 24-2 upon the pressing of the medical liquid.

Figure 3:
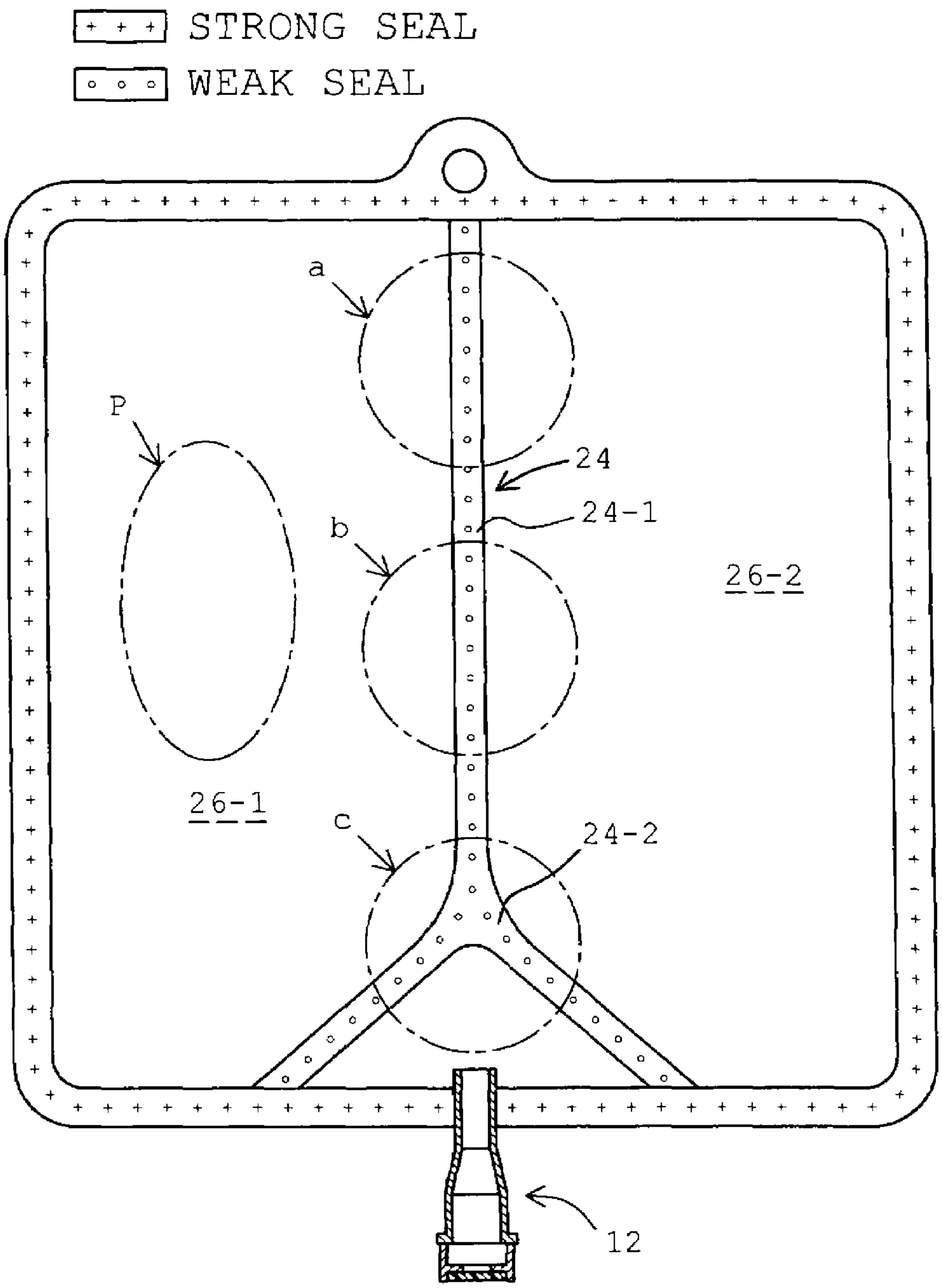
Fig.3 PRIOR ART
FIG. 3 is a plan view of a conventional multi-chamber container.

FIG. 3 illustrates a prior art medical bag with no provision of any additional strong seal in the present invention. In this prior art medical bag, the inventors of the present invention executed opening test by several testers. The instruction to the testers was that the pressing of the medical bag should be done at the central part P of the left-handed partition 26-1 adjacent the second portion 24-1 of the weak seal 14. However, due to no provision of means for restriction of the direction of the transmission of the inflated deformation, an inevitable variation is occurred as to the location where the opening is occurred, as typically illustrated by the three position a, b or c. The initial occurrence of the opening at the position a or b makes the liquids between the partitions 26-1 and 26-2 to be mixed. However, the initial opening at the position c occurs at a significant rate and, in this case, there will be a chance that an infusion is done at a non-mixed state or insufficient mixed state. The provision of the additional strong seals 30-1 and 30-2 according to the present invention makes it sure that the separation occurs initially at the first portion 24-1 of the weak seal, resulting in a positive mixture of the medial liquids prior to the commencement of infusion operation.

Figure 4:
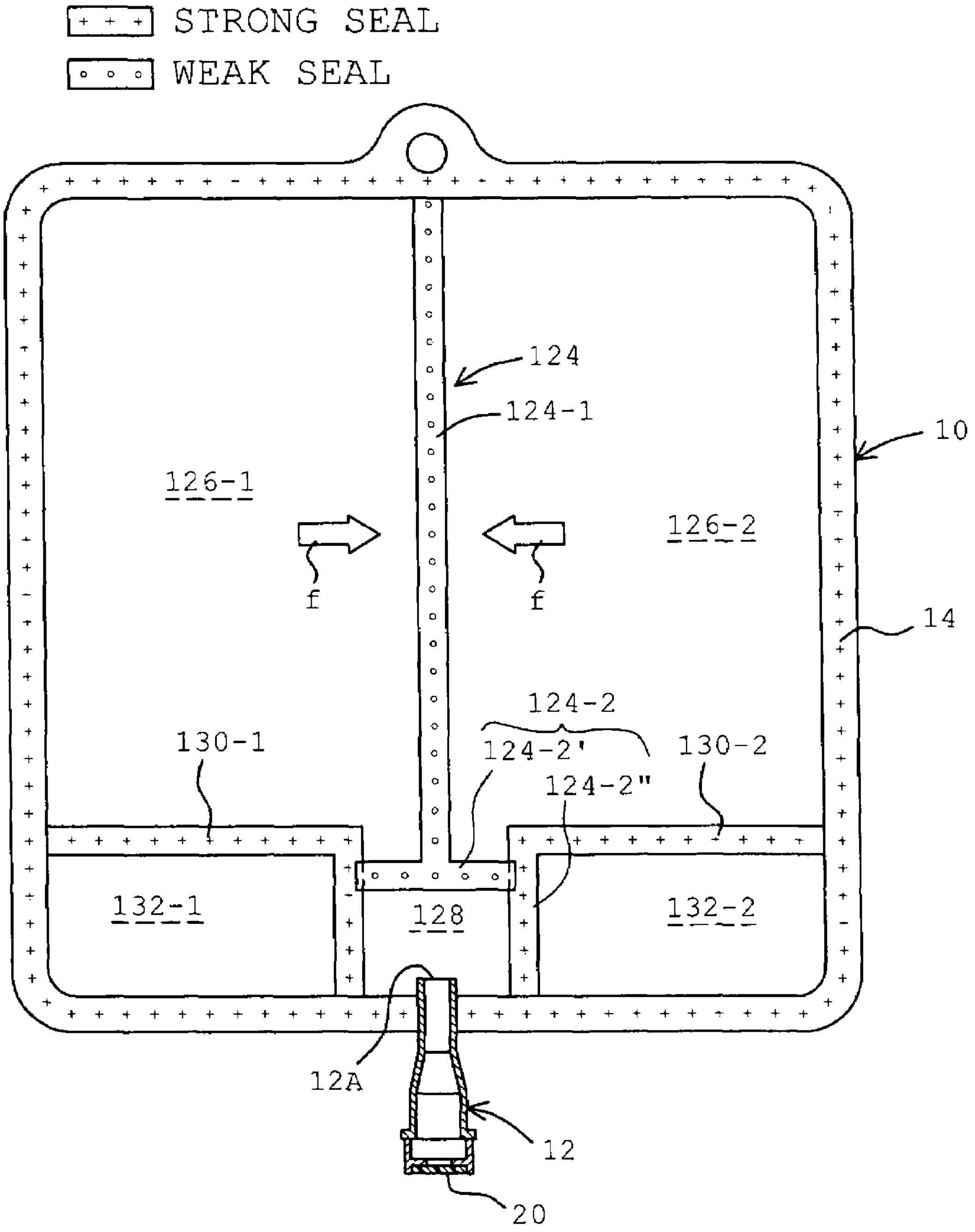
FIG. 4 is a plan view of a multi-chamber container according to another embodiment of the present invention.

FIG. 4 illustrates second embodiment of the present invention, where the first weld 124 has a first portion 124-1 and a second portion 124-2. The first portion 124-1 extends between the left-handed and right-handed partitions from the upper periphery (strong seal 14) of the medical bag 10 to a location adjacent to and faced with the outlet port 12. The first portion 124-1 (a weak seal) is separable along its entire length. The second portion 124 of the first weld has separable parts 124-2' (weak seals) extending left-handed and right-handed directions from the first portion 124-1 and non-separable parts 124-2" (strong seals) extending, at both sides of the outlet port 12, from the separable parts 124-2' to the bottom periphery (strong seal 14) of the medical bag 10. The additional seals 130-1 and 130-2 (second welds of the claimed invention) are for mainly directing the inflated deformation of the medial bag to the first portion 124-1 of the first weld as shown by the arrows f, as generated when opening the medical bag and extend, at first, upwardly, as the extensions of the non-separable parts 124-2" and, then, horizontally in a manner that small chambers 132-1 and 132-2 are created, which are independent not only from the partitions 126-1 and 126-2 but also from the intermediate chamber 128.

In a medical bag of this embodiment, a high temperature welding is done for obtaining the seals 14, 124-2", 130-1 and 130-2, to obtain non-separable seals (strong seals). Therefore, in this embodiment, a welding head for a strong seal is advantageously of a shape, which forms simultaneously the non-separate portion 124-2" of the first weld and the additional strong seals 130-1 and 130-2 as the second weld. After the execution of the high temperature welding, a low temperature welding is executed for obtaining the separable welded portions 124-1 and 124-2'. The deformation (inflation) as generated by the pressing of the partition 126-1 or 126-2 is, as shown by arrows f, mainly transmitted to the weak seal 124-1 horizontally separating the partitions 126-1 and 126-2. Therefore, the separation of the weak seal 124-1 occurs at first, resulting in the mixing of the medicines between the partitions 126-1 and 126-2. Then, the medical bag is subjected to a second stage pressing in a manner that the weak seal 124-2' is separated, resulting in an introduction of the mixed medicines into the outlet port 12.

Figure 5:
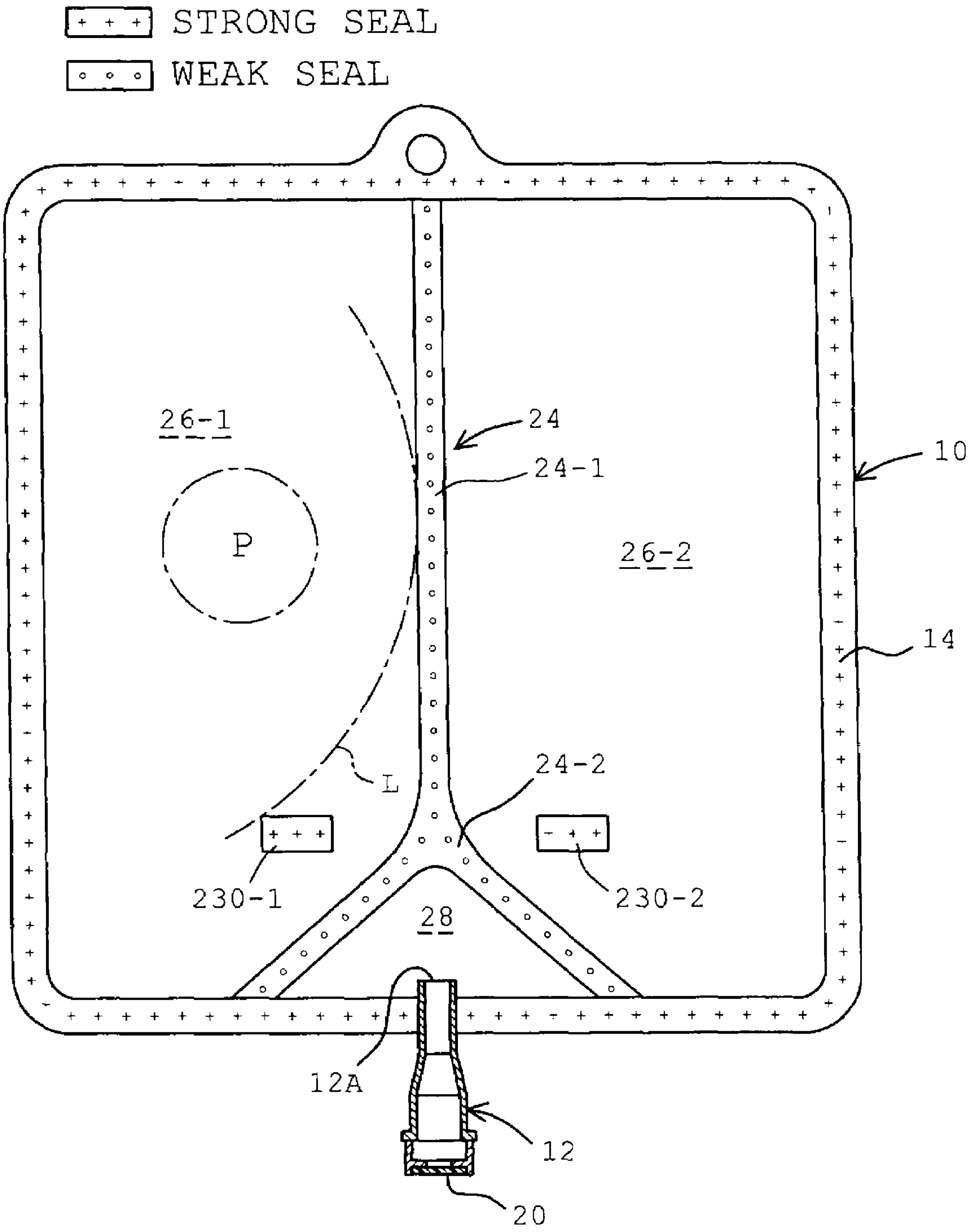
FIG. 5 is a plan view of a multi-chamber container according to further another embodiment of the present invention.

FIG. 5 illustrates a third embodiment of the present invention, wherein, as similar to the first embodiment in FIG. 1, the weak seal 24 has a first portion 24-1 extending downwardly between the left-handed and right-handed partitions 26-1 and 26-2 from the upper periphery (strong seal 14) of the medical bag to the location adjacent to and faced with the open end 12A of the outlet port 12 and a second portion 24-2 extending from the first portion 24-1 in bilateral directions under a bifurcated shape toward the lower periphery of the medical bag. A pair of additional strong seals 230-1 and 230-2 is arranged on both sides of the outlet port 12 in a manner that the upper and lower layers of the medical bag are welded non-separably. In this embodiment, the additional strong seals 230-1 and 230-2 have relatively short length in a manner that they are spaced not only from the peripheral strong seal 14 but also from the first weld 24. Therefore, this third embodiment lacks in parts corresponding to the small chambers 32-1 and 32-2 separated not only from the partitions 26-1 and 26-2 but also from the third chamber 28 in the first and second embodiment and, therefore, an increase amount of medical liquids to be stored in the partitions 26-1 and 26-2 are obtained. The additional strong seals 230-1 and 230-2 are arranged at locations, whereat the transmission of the inflated deformation to the second portion 24-2 of the weak seal 24 is restricted, as obtained when the medical liquid in one of partitions 26-1 and 26-2 is pressed for opening the medical bag 10. In FIG. 5, P illustrates a location at the center of the left partition 26-1 where the pressing by the palm is done, while L illustrates a front edge of the resultant inflated deformation of the bag, which is just transmitted to the additional strong seal 230-1. The provision of the additional strong seal 230-1 functions to prevent the bag inflated deformation from being transmitted to the second portion 24-2 of the weak seal 24. Contrary to this, the inflated deformation is instantly transmitted to the first portion 24-1 of the weak seal 24. In other words, the medical bag is opened initially at the first portion 24-1 of the weak seal 24, which causes the medicines to be mixed between the left-handed and the right-handed partitions 26-1 and 26-2. Then, the pressing of the medical bag is further processed in a manner that the second portion 24-2 is separated and opened, so that the mixed medicines are directed to the outlet port 12.

In the above embodiments, a weld between the faced layers of the medical bag functions to restrict the transmission of the inflated deformation as generated by the pressure to the medical fluid. However, in place of the weld, any alternative means, which functions in a similar way, can be employed.

The invention claimed is:

1. A medical bag, comprising:

a first flexible film;

a second flexible film;

at least one peripheral non-separable weld that welds a peripheral portion of the first flexible film to a peripheral portion of the second flexible film to define a chamber for holding a medical composition;

an outlet port mounted to the medical bag for discharging the medical composition from the chamber;

at least one separable weld that welds a first interior portion of the first flexible film to a first interior portion of the second flexible film to define at least a first partition, a second partition and a third partition within the chamber; and at least one interior non-separable weld that welds a second interior portion of the first flexible film to a second interior portion of the second flexible film;

wherein:

the first partition holds a first medical liquid;

the second partition holds a second medical liquid;

the outlet port communicates between the third partition and an exterior of the medical bag;

the at least one separable weld comprises a first section separating the first partition from the second partition;

the at least one separable weld comprises a second section separating the first partition from the third partition;

the at least one separable weld comprises a third section separating the second partition from the third partition;

the at least one interior non-separable weld is provided in proximity to the second and third sections of the at least one separable weld, so that when the medical bag is deformed, the first section of the at least one separable weld breaches before the second and third sections, allowing the first and second medical liquids to mix before contacting the outlet port;

the first section of the at least one separable weld extends from a first location on the exterior separable weld to an interior location of the chamber opposite from the outlet port;

the second section of the at least one separable weld extends from the interior location of the chamber opposite from the outlet port to a second location on the exterior separable weld adjacent to the outlet port;

the third section of the at least one separable weld extends from the interior location of the chamber opposite from the outlet port to a third location on the exterior separable weld adjacent to the outlet port;

the second and third locations on the exterior separable weld are astride the outlet port; and the at least one interior non-separable weld comprises a first interior non-separable weld adjacent to the second section of the at least one separable weld and a second interior non-separable weld adjacent to the third section of the at least one separable weld.

2. The medical bag of claim 1, wherein:

the first interior non-separable weld overlaps the second section of the at least one separable weld; and the second interior non-separable weld overlaps the third section of the at least one separable weld.

3. The medical bag of claim 1, wherein at least a portion of the at least one interior non-separable weld extends in a direction transverse to the first section of the at least one separable weld.

4. A medical bag, comprising:

a first flexible film;

a second flexible film;

at least one peripheral non-separable weld that welds a peripheral portion of the first flexible film to a peripheral portion of the second flexible film to define a chamber for holding a medical composition;

an outlet port mounted to the medical bag for discharging the medical composition from the chamber;

at least one separable weld that welds a first interior portion of the first flexible film to a first interior portion of the second flexible film to define at least a first partition, a second partition and a third partition within the chamber; and at least one interior non-separable weld that welds a second interior portion of the first flexible film to a second interior portion of the second flexible film;

wherein:

the first partition holds a first medical liquid;

the second partition holds a second medical liquid;

the outlet port communicates between the third partition and an exterior of the medical bag;

the at least one separable weld comprises a first section separating the first partition from the second partition;

the at least one separable weld comprises a second section separating the first partition from the third partition;

the at least one separable weld comprises a third section separating the second partition from the third partition;

the at least one interior non-separable weld is provided in proximity to the second and third sections of the at least one separable weld, so that when the medical bag is deformed, the first section of the at least one separable weld breaches before the second and third sections, allowing the first and second medical liquids to mix before contacting the outlet port;

the at least one interior non-separable weld comprises a first interior non-separable weld extending into the chamber from a first location on the at least one peripheral non-separable weld;

the at least one interior non-separable weld comprises a second interior non-separable weld extending into the chamber from a second location on the at least one peripheral non-separable weld;

the first and second locations on the at least one peripheral non-separable weld are astride the outlet port;

the first section of the at least one separable weld extends from a third location on the exterior separable weld to an interior location of the chamber opposite from the outlet port;

the second section of the at least one separable weld extends from the interior location of the chamber opposite from the outlet port to the first interior non-separable weld; and the third section of the at least one separable weld extends from the interior location of the chamber opposite from the outlet port to the second interior non-separable weld.

5. The medical bag of claim 4, wherein:

at least a portion of the first interior non-separable weld extends substantially parallel to the first section of the at least one separable weld; and at least a portion of the second interior non-separable weld extends substantially parallel to the first section of the at least one separable weld.

6. The medical bag of claim 5, wherein:

at least a portion of the first interior non-separable weld extends substantially transverse to the first section of the at least one separable weld; and at least a portion of the second interior non-separable weld extends substantially transverse to the first section of the at least one separable weld.

7. The medical bag of claim 6, wherein:

the first interior non-separable weld extends from the first location on the peripheral non-separable weld to a further location on the peripheral non-separable weld to define a space within the chamber that is separate from the first, second and third partitions; and the second interior non-separable weld extends from the second location on the peripheral non-separable weld to a further location on the peripheral non-separable weld to define a space within the chamber that is separate from the first, second and third partitions.

8. A method for dispensing a medical composition, comprising:

providing the medical bag of claim 1;

deforming the medical bag to breach the first section of the at least one separable weld and cause mixing of the first medical liquid and the second medical liquid to prepare the medical composition;

further deforming the medical bag to breach at least one of the second and third sections of the at least one separable weld to bring the medical composition into communication with the outlet port;

dispensing the medical composition from the medical bag via the outlet port.

9. A method for dispensing a medical composition, comprising:

providing the medical bag of claim 4;

deforming the medical bag to breach the first section of the at least one separable weld and cause mixing of the first medical liquid and the second medical liquid to prepare the medical composition;

further deforming the medical bag to breach at least one of the second and third sections of the at least one separable weld to bring the medical composition into communication with the outlet port;

dispensing the medical composition from the medical bag via the outlet port.

* * * * *